US010743885B2

(12) United States Patent
Menovsky et al.

(10) Patent No.: US 10,743,885 B2
(45) Date of Patent: Aug. 18, 2020

(54) CLIP FOR ANEURISM

(71) Applicant: NEOS SURGERY, S.L., Cerdanyola del Vallès, Barcelona (ES)

(72) Inventors: Tomas Menovsky, Antwerp (BE); Thorsten Asal, Kaiserslautern (DE); Markus Steffens, Winnweiler (DE); Salvador Llas Vargas, Lleida (ES); Pau Garcia Roig, Girona (ES); Montserrat Charles-Harris Ferrer, Barcelona (ES); Marc Serrahima Tornel, Sant Cugat del Valles Barcelona (ES); Martin Gurka, Landau (DE); Thorsten Becker, Hermersberg (DE)

(73) Assignee: NEOS SURGERY, S.L., Cerdanyola del Vallés (ES)

( * ) Notice: Subject to any disclaimer, the term of this patent is extended or adjusted under 35 U.S.C. 154(b) by 312 days.

(21) Appl. No.: 15/540,635

(22) PCT Filed: Dec. 28, 2015

(86) PCT No.: PCT/ES2015/070957
§ 371 (c)(1),
(2) Date: Jun. 29, 2017

(87) PCT Pub. No.: WO2016/107952
PCT Pub. Date: Jul. 7, 2016

(65) Prior Publication Data
US 2018/0008275 A1  Jan. 11, 2018

(30) Foreign Application Priority Data

Dec. 30, 2014 (ES) .................................. 201431951

(51) Int. Cl.
*A61B 17/10* (2006.01)
*A61B 17/122* (2006.01)
(Continued)

(52) U.S. Cl.
CPC ........ *A61B 17/1227* (2013.01); *A61B 17/128* (2013.01); *A61B 2017/00477* (2013.01);
(Continued)

(58) Field of Classification Search
CPC ..... A61B 17/122; A61B 17/10; A61B 17/128; A61B 17/1285; A61B 17/1227;
(Continued)

(56) References Cited

U.S. PATENT DOCUMENTS 4,147,167 A * 4/1979 Hickmann .............. A61F 2/141
606/107
4,324,248 A * 4/1982 Perlin ................ A61B 17/1227
24/545
(Continued)

FOREIGN PATENT DOCUMENTS

WO   2004/080275 A2   9/2004
WO   2007/124579 A1   11/2007

OTHER PUBLICATIONS

Search Report of Spanish Patent Application No. 201431951, dated Oct. 14, 2015.
(Continued)

*Primary Examiner* — Vi X Nguyen
(74) *Attorney, Agent, or Firm* — Sughrue Mion, PLLC (57) ABSTRACT

Clip for an aneurism suitable for being implanted into tissue in which an aneurism has formed and carrying out a tight closure of the aneurism. The clip includes a pair of claw members (2a, 2 b) non-metallic material, the claw members provided with an articulated joining mechanism (3), which allows rotation of the pair of claw members around a pivot (4) which interlocks them. The clip can adopt at least one opening position (A) and one closure position (B). The clip has at least one spring element (6) at least partially housed in the clip which bends to arrange the clip in closure position which includes at least one flexible (7) and elastic element with a section with arced configuration (8), press-fitted with
(Continued)

two opposing ends (9a, 9b) each one exerting pressure on a different claw member both in the opening and in the closure position.

34 Claims, 7 Drawing Sheets

(51) Int. Cl.
    *A61B 17/128*     (2006.01)
    *A61B 90/00*     (2016.01)
    *A61B 17/00*     (2006.01)

(52) U.S. Cl.
    CPC ............... *A61B 2017/00738* (2013.01); *A61B 2017/00862* (2013.01); *A61B 2090/3966* (2016.02)

(58) Field of Classification Search
    CPC .. A61B 2017/00477; A61B 2017/0488; A61B 2017/00862; A61B 2017/00738
    See application file for complete search history.

(56) References Cited

U.S. PATENT DOCUMENTS

| | | |
|---|---|---|
| 4,813,107 A | 3/1989 | Cetrone |
| 4,932,955 A | 6/1990 | Merz et al. |
| 2004/0254596 A1 | 12/2004 | Kuester, III |
| 2006/0195125 A1 | 8/2006 | Sakakine et al. |
| 2011/0224700 A1 | 9/2011 | Schmidt et al. |
| 2013/0245653 A1 | 9/2013 | Litherland |

OTHER PUBLICATIONS

International Search Report of PCT/ES2015/070957, dated Apr. 26, 2016. [PCT/ISA/210].

Written Opinion of PCT/ES2015/070957, dated Apr. 26, 2016. [PCT/ISA/237].

\* cited by examiner

CLIP FOR ANEURISM

CROSS REFERENCE TO RELATED APPLICATIONS

This application is a National Stage of International Application No. PCT/ES2015/070957 filed Dec. 28, 2015, claiming priority based on Spanish Patent Application No. P201431951, filed Dec. 30, 2014, the contents of all of which are incorporated herein by reference in their entirety.

TECHNICAL SECTOR OF THE INVENTION

The invention relates to a clip for an aneurism, suitable for being implanted into tissue in which an aneurism has formed and carrying out a tight closure of the aneurism.

BACKGROUND OF THE INVENTION

When an aneurism is detected in the tissue of a body, principally in a blood vessel, causing the rupture of said aneurism should be avoided, which would entail a hemorrhage in the patient which could involve serious consequences and even death. It is therefore essential to be able to act when an aneurism is detected and carrying out a tight closure on the tissue which avoids the aneurism being able to open.

With this aim, clips for aneurisms of various sizes are known which allow, by means of an applicator, a tight closure of the aneurism to be carried out. From among the most well-known, the clip described in the patent document U.S. Pat. No. 4,360,023 stands out, formed by a single piece provided with flexible elastic means. However, the manufacture of this clip is complicated to automate and it is principally carried out by hand and the fact that it comprises metallic materials creates artifacts which make the subsequent tracking of the aneurism difficult by means of imaging techniques.

It is therefore necessary to provide clips for an aneurism which do not create artifacts, consequently clips for an aneurism like the one described in the patent documents U.S. Pat. No. 4,671,281 and US20130245653 are known, which describe a non-metallic clip in which both claw members are formed in a single piece, said piece being provided with a locking stop for the clip in a closed position. However, this type of clip is not only difficult to install, but it is also not very reliable for maintaining sufficient pressure during the entire life of the patient in order to avoid the closure becoming loose.

Clips for aneurisms are also known like the one described in the patent document EP0346084 in which the articulated claw members are manufactured with a synthetic resin or with ceramic and the spring part is made of a synthetic resin. These types of clips notably reduce the artifacts caused during tomography by means of X-rays or magnetic resonance. However, the manufacture of these types of clips is complex since the claw members and the spring have to be perfectly joined, and moreover, the elastic means of the clip are exposed.

The patent document U.S. Pat. No. 4,324,248 A describes a clip for micro-surgery which allows the occlusion of small blood vessels, formed by a single piece folded over itself which determines two claws subjected to the influence of an elastic element in the general form of a torsion spring.

It is therefore an object of the present invention to make known a clip for an aneurism which allows the easy manufacture thereof and allows tight and secure closure of an aneurism, maintaining the aneurism sufficiently closed during the entire life of the patient.

Another object of the present invention is to make known a kit formed by a clip for an aneurism and an applicator which allows the clip to be inserted in an easy and versatile manner into places which are difficult to access.

It is also an object of the present invention to make known an alternative to the known clips for aneurisms.

DESCRIPTION OF THE INVENTION

The clip for an aneurism of the present invention is one that comprises a pair of claw members of non-metallic material, for example a polymeric material, said claw members being provided with means for the articulated joining of the claw members which allows the rotation of the pair of claw members around a pivot which interlocks them, a resistance arm and a power arm being distinguished on each claw member, being configured such that the clip can adopt at least: an opening position, in which the resistance arms of the claw member are separated; and a closure position, in which the resistance arms of the claw members are applied to each other; the clip being provided with at least one spring element which bends to arrange the clip in the closure position. Of course, each claw member can be formed by a single element or can be formed by the firm joining of various elements, for example different materials, these being firmly joined to each other during the manufacturing phases of the claw members, for example by means of over-injection.

In essence, the clip is characterized in that the at least one spring element is at least partially housed in the clip and comprises an element flexible and elastic with a section with arced configuration, press-fitted with two opposing ends each exerting pressure on a different claw member both in the opening and in the closure position, and housed in the clip such that the spring element(s) can be introduced into the pre-tensioned claw members and remain completely confined and protected by the claw members, without protruding from the profile of the clip, thereby allowing the spring element(s) to be easily positioned in a secure manner without necessarily having to solder or thermoform the clip. It is envisaged that the flexible element is at least partially housed in the clip, being in part inserted in the claw members without protruding from the profile of the clip, that is to say, from the volume in which the clip is contained, specifically the pair of interlocked claw members such that the flexible element is positioned within the clip without protruding, being protected by the clip, specifically by the claw members.

According to another embodiment variant, the at least one spring element is completely housed in the clip such that the flexible element of the at least one spring element is inserted in one of the claw members, for example, in an opening, of said claw member, the flexible element, or the entire spring element, thus being incorporated in the interior of the claw member without it being necessary to provide a different housing for the flexible element which would involve increasing the size of the clip or the flexible element protruding from the profile of the clip. Of course, it is considered that in different embodiments of the clip there is only one spring element formed by a flexible element, a spring element formed by various flexible elements and various spring elements, for example two, one in each claw member which can each be formed by one or a plurality of flexible elements of which at least one spring element is housed in a claw member. Preferably, the flexible element of the at least one spring element is housed in the resistance arm of a claw member, thus utilizing the thickness of the resistance arm to house and integrate the flexible element. It is similarly envisaged that when there are various spring elements formed by one or a plurality of flexible elements, at least one of said flexible elements is housed, that is to say, inserted into the resistance arm of a claw member, that is, the arm of the claw member which carries out the clipping of the aneurism after being closed as a result of the at least one spring element of the clip.

According to another embodiment variant, the flexible element has an arced shape without being or forming a surpassed or horseshoe arc, that is, the curve thereof does not exceed 180° both in the opening position A and in the closure position B of the clip, thus allowing the functioning thereof in the manner of a leaf spring exerting force in the essentially longitudinal direction thereof.

It is also made known that the flexible element is oblong, the opposed ends of the flexible element being retained on a different claw member, thus being able to occupy a reduced space in the interior of the claw members and suitably actuate the clip.

In a variant of interest, the flexible element is laminar, thus being able to carry out a distribution of the forces which said flexible element exerts over the entire width of the clip.

In an embodiment variant, the thickness (e) of the flexible element, the length of the clamped surface (b) and the elastic module (E) of the material with which the flexible element is manufactured are related by means of the expression:

$$e = \sqrt[3]{\frac{b}{\beta E}}$$

where (β) is a geometric factor with value 7.5. With this relation, the clamped surfaces exerts a force of 180 grams on the aneurism, sufficient to stop the flow of blood.

It is also made known that the width of the flexible element is between 5 and 10 times the thickness thereof and the chord length of the arc of the flexible element in the closure position is between 20 and 60 times the thickness thereof, thus allowing the flexible element, which has small dimensions, to be able to be inserted into the clip and allow sufficient elastic energy to be stored in order to be maintained within the elastic range both in the opening and closure position of the clip.

In an embodiment variant when the material of the flexible element is Endolign aligned with the fiber, the thickness (e) of the flexible element is between 0.5 and 0.05 mm, the width (a) of the flexible element is less than 2 mm and the chord length (I) of the arc of the flexible element in the closure position B is between 4 and 12 mm, being able to advantageously fit in the clip with reduced dimensions with a clamped surface length of 9 millimeters, at the same time allowing the clip to exert sufficient force on the aneurism.

It is also made known that the radius between the support point of the flexible element and the center of the rotational pivot is between 0.5 and 3 millimeters such that the force which the flexible element exerts is transferred in an efficient manner to the clip.

In another embodiment variant, the spring element(s) comprise two flexible elements each one arranged housed in a corresponding claw member, that is to say, within the corresponding clamp member, thus allowing the force of the clip to be distributed among the two claw members. Of course, it is considered that the clip is only provided with one flexible element, the number thereof also being able to be increased to two, four or more. When the clip comprises two flexible elements, the claw members can be equal, thus advantageously using the same molds for both claw members and subsequently joining them by means of an articulated joining formed, for example, by a rod riveted at the ends thereof.

It is also made known that each one of the claw members is formed by a single piece, being able to be formed by means of a mold and without it being necessary to have to assemble different components in order to form each one of the claw members. This characteristic facilitates the manufacture and assembly of the clip whilst reducing the number of components, in addition to facilitating the distribution of tensions in the clip, thus avoiding the appearance of weak points. It is emphasized that the clips for an aneurism have a reduced size, therefore during the assembly thereof pieces with reduced size have to be handled, as a result it is advantageous for each claw member to be formed by a single piece. Of course, it is also envisaged that said single piece is a piece which during the manufacturing process thereof had included various elements which are ultimately joined in a fixed manner, for example by means of over-injection, after said manufacturing process, thus ultimately forming a single piece. These elements can have different mechanical properties such that they can form claw members with the shapes which are most suitable, for example in order to obtain longer and thinner power arms.

In another embodiment variant, considering the horizontal and frontal cut planes thereof orthogonal to each other and which are intersected in the center of the pivot, the flexible element(s) are placed, each one, in the same quadrant both in the opening and in the closure position, advantageously allowing the forces, which are applied on the power members, to be concentrated.

It is also made known that at least one of the claw members comprises a lobe, one of the opposed ends of the flexible element being retained in an indentation of the perimeter of the lobe such that the flexible element is fitted and can actuate the clip.

It is also made known that at least one of the claw members comprises an opening, which can have an ogive shape, configured in the manner of a groove which receives and houses a corresponding flexible element such that the flexible element is housed within the clip without protruding. The opening can be provided with an edge for retaining one of the opposed ends of the flexible element. In this way, the flexible element being retained on each one of the opposed ends thereof by a different claw member, for example by the indentation of the perimeter of the lobe of a claw member and by the edge of the ogive opening in the other claw member, the flexible element is duly confined in the interior of the clip and acts by storing and releasing potential elastic energy for the actuation of the clip.

It is also made known that the claw members are provided with clamping surfaces complementary to each other, that is to say, that in the closure position they fit into each other and are provided with roughness in the form of peaks and troughs perpendicular to the longitudinal direction of the clip such as undulations or serrated teeth which improve the grip of the clip whilst facilitating the demolding thereof during the manufacture thereof.

In another embodiment variant, the opening, which can be in an ogive shape, is provided with lateral retention means such as a lateral tooth or wall in order to avoid the flexible element laterally protruding from said ogive opening in which it is housed. However, these lateral retention means are not essential because since the flexible element is always tensioned, both in the opening position and in the closure position of the clip, it is still solidly inserted and press-fitted within the clip. However, for greater security, lateral retention means can be provided. These lateral retention means are useful especially when the flexible element is not laminar, for example if it is formed by one or a plurality of rods which can be curved in the direction of the exterior of the clip.

In another variant of interest, the clip comprises a subsequent channel between the claw members for introducing the flexible element. In this way, the assembly of the clip can be automated, subsequently introducing the flexible element by means of said channel and tightening it until it is fitted and retained between the claw members.

According to another embodiment variant, the power arms of the claw members comprise stop surfaces adapted for being applied to each other in the opening position, limiting the opening of the clip, and separated in the closure position. By means of the separation of these stop surfaces, the maximum opening, which the clip can adopt, can be predefined.

It is also made known that both in the opening position and in the closure position, the straight lines tangential to the ends of the section with arced configuration of the flexible element determine an angle greater than 90 degrees, allowing the flexible element to be housed within the clip at all times without protruding. When the flexible element is housed in the opening of a claw member, the height of this opening is designed such that it avoids retaining the section with arced configuration of the flexible element, therefore, the height of the opening is always greater than the height of the arc which the flexible element determines when tightened.

In another embodiment variant, the section with arced configuration of the flexible element has the same direction of concavity both in the opening position and in the closure position of the clip, that is to say, the section with arced configuration is maintained either convex or concave in both positions, in other words, it always protrudes transversally towards the same side of the straight line which joins the ends of the section with arced configuration, thus allowing the flexible element to be pressed fitted at all times between the claw members.

According to another characteristic of the invention, the material of the claw members and of the spring element(s) of the clip is biocompatible and comprises, for example PEEK such that it can be directly implanted into human beings for clamping an aneurism. It is also envisaged that if some material were not directly biocompatible, this could be encapsulated in a biocompatible medium.

It is also made known that the flexible element comprises a material with continuous carbon fiber which is biocompatible and allows sufficient force to be carried out so as to close the clip on the aneurism. Of course, other flexible elements, which contain carbon fiber or encapsulated fiber glass, can be used since the flexible element is housed in the claw members and therefore never protrudes from the clip. It is also possible to use a metallic element if it were required.

In a variant of interest, the clip also comprises loads of a radiopaque material or a piece marked with a material radiopaque to the radiations which are used in the medical field for carrying out diagnostic imaging such as X-rays. Preferably, the loads of material radiopaque to X-rays can be compounds such as barium sulfate, zirconium oxide or bismuth oxychloride. These loads of radiopaque material can be compounds or solutions which are mixed with the polymer during the manufacture of the claw members of the clips, both before and during the injection phase, for example both being in a liquid or viscous phase. The proportion of the mixture of polymer and the radiopaque compound depends on the visibility which is desired to be given to the clip in the visualizations when carrying out the diagnostic imaging. In this way, the clip is slightly visible without it creating artifacts which obscure the aneurism in the image such that the specialist who analyzes the image can see both the aneurism and the clip which closes it. Preferably, the loads of opaque material are uniformly distributed on the at least one claw member such that the shape of the said claw member is visible when carrying out the diagnostic imaging. Of course, when the loads of opaque material are uniformly distributed on both claw members, this allows the shape of the clip to be uniformly visualized in the image obtained when diagnostic imaging is carried out. Preferably the marked piece will be made of a material radiopaque to X-rays such as tantalum or titanium, allowing the clip to be identified in a diagnostic imaging process such that the clip can be identified, but without this producing artifacts which can distort the image. Of course, it is envisaged that both the loads of radiopaque material and the pieces marked with radiopaque material are radiopaque to the radiations which allow images to be obtained by means of other diagnostic imaging techniques which can be varied as a function of the technique.

It is also made known that the marked piece can comprise a microsphere embedded in at least one of the claw members during the manufacture stage thereof such that the image with which the clip is identified is the same irrespective of the position of the clip since it is always identified with a circle.

In another embodiment variant, the marked piece comprises a metal filament embedded in at least one of the claw members, preventing artifacts being produced when a thread-like shadow is present.

In another variant of interest, the marked piece comprises a washer inserted between the two claw members, advantageously allowing the washer to be inserted during the assembly phase of the clip, it being able to be decided at that moment whether it is desired for the clip to be completely radiotransparent or to include a marked piece.

It is also made known that in one embodiment variant the marked piece is the pivot of the clip itself, thus avoiding having to add additional elements which act in the manner of the marked piece.

In another embodiment variant, the marked piece is a metallic inlay in at least one of the two claw members, this metallic inlay being able to be applied by means of ultrasound.

In another embodiment variant, the thickness of the claw member is less at the frontal end thereof than at the rear end thereof, allowing the closure force, which the claw members exert on the aneurism, to be better concentrated. Furthermore, the clip can be provided with lateral recesses on both sides to help the surgeon see during the implantation thereof.

A kit formed by one or a plurality of clips and an applicator for handling and articulating said clip are also made known. The clip comprises support areas on the power arms of the claw members adapted for cooperating with the applicator such that the clip rotates from the closure position to the opening position thereof when the applicator exerts pressure on said support areas. In this way, the surgeon easily handles the clip which usually has very small dimensions.

In another variant of the kit of interest, the kit is characterized in that at least one of the support areas of the clip comprises a cup provided with two straight parallel surfaces, adapted for receiving an essentially hemispheric end of the applicator provided with a set of straight parallel faces forming a polygonal prism with the end rounded. In this way, the clip can be advantageously actuated at different angles according to how the straight parallel faces of the applicator are against the two straight parallel surfaces of the cups. Typically, the clip comprises two cups, one on each power arms of the claw members adapted for receiving two essentially hemispheric ends of the applicator in the manner of projections. Of course, it is possible to use the clip with other applicators as well as use this applicator with other clips. Although the cup of the clip is normally an opening and the hemispheric end of the applicator is a projection, they could be arrange the other way around. The cup could also be on the applicator and the hemispheric end on the clip.

Advantageously, the separation between the two straight parallel surfaces of the cup of the clip is greater than the separation between the straight parallel faces of the essentially hemispheric end of the applicator, thus allowing the clip to be able to rotate in controlled steps when certain lateral pressure is exerted against the clip when it is held by the applicator.

BRIEF DESCRIPTION OF THE DRAWINGS

In order to complement the description and with the aim of facilitating the understanding of the characteristics of the invention, the present specification is accompanied by a set of drawings in which the following is depicted in an illustrative and non-limiting manner.

DETAILED DESCRIPTION OF THE DRAWINGS

Figure 1:
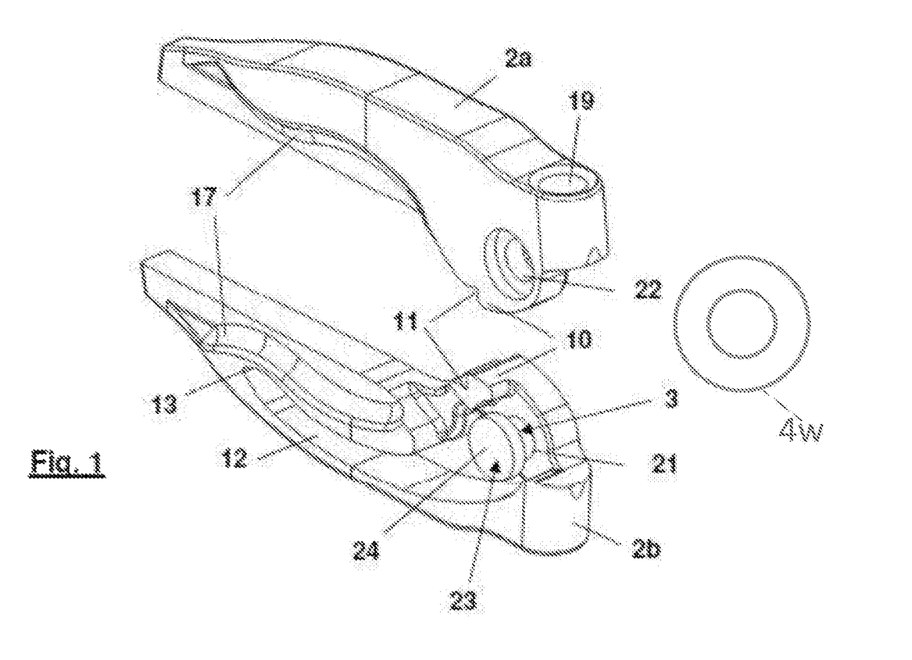
FIG. 1 depicts a perspective view of the separated claw members which will form a clip of the present invention.

FIG. 1 shows a pair of claw members 2a, 2b of a non-metallic material, for example a biocompatible polymeric material such as for example PEEK which form the clip 1 of the present invention. When this material is biocompatible, it allows the application thereof in the interior of the body, closing an aneurism. The material is also sufficiently resistant so as not to degrade in the interior of the body.

Each one of the claw members 2a, 2b can be manufactured separately by means of over-injection of PEEK, that is to say, initially they are separated pieces, being able to be subsequently assembled to form the clip 1. Of course, each claw member 2a, 2b can be formed by various fixedly joined elements, for example various elements of materials which can have different mechanical properties such as different rigidity. These various elements of materials are fixedly joined during the manufacture of the claw member 2a, 2b, for example when the claw member 2a, 2b is formed by means of over-injection of PEEK on a PEEK nucleus with continuous carbon fiber. In this way, the manufacture of clips of various shapes is possible, for example clips with more elongated and slimmer claw members 2a, 2b.

Figure 5A:
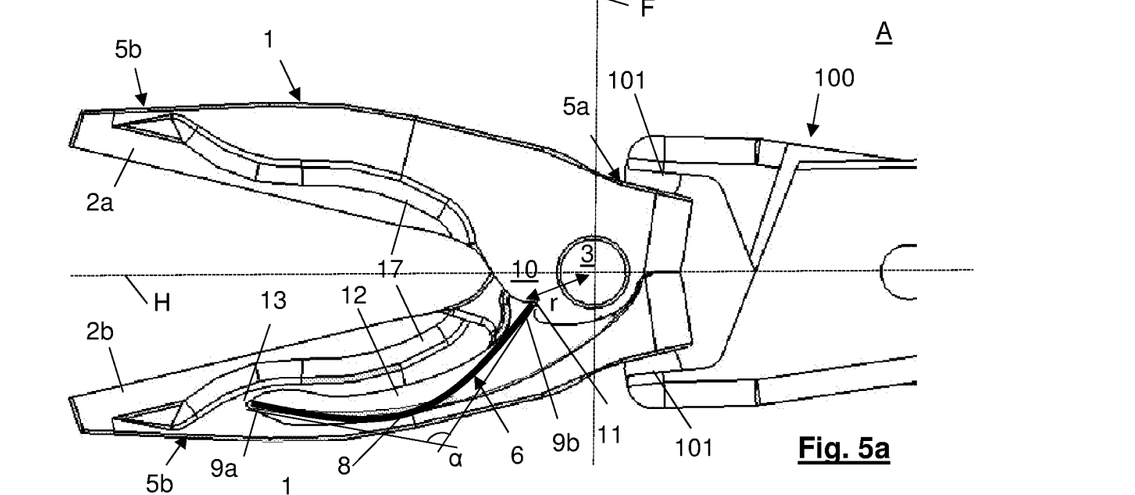
FIGS. 5a to 5c depict a closure sequence of the clip of FIG. 3 by means of an applicator.
Figure 5B:
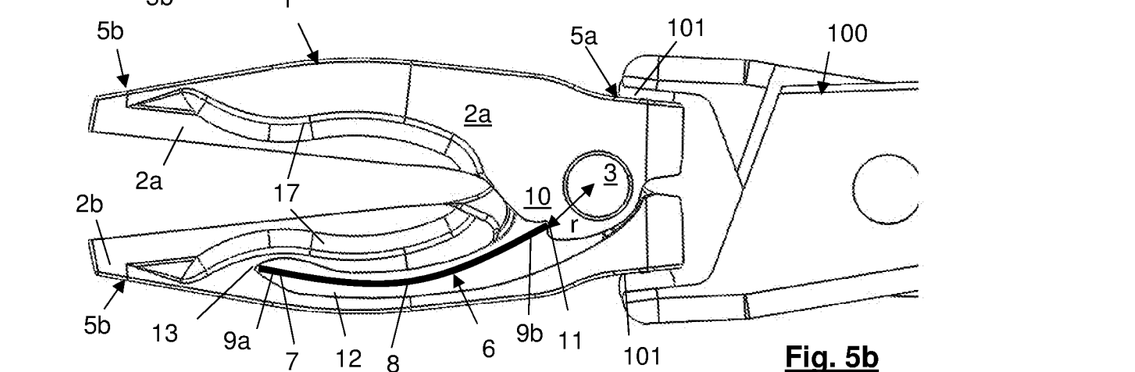
Figure 5C:
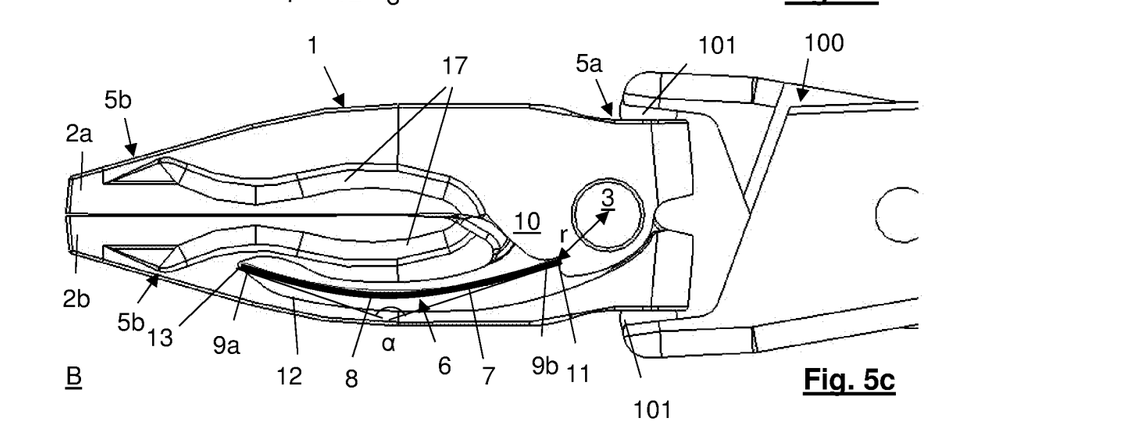

The pair of claw members 2a, 2b shown in FIG. 1 are ready to be articulatedly joined to each other to form a clip 1 provided with a rotational pivot 4, and house one or a plurality of spring elements 6, determining each claw member 2a, 2b which allows the clip 1 to pass from an opening position A which is illustrated for example in FIG. 5a, in which an external force is exerted on the clip 1, to a closure position B which is illustrated for example in FIG. 5c, when said external force on the clip 1 is removed and can thus be closed on tissue with an aneurism to isolate the aneurism from the rest of the tissue such as a blood vessel.

Both claw members 2a, 2b are provided with respective openings 12 for housing the spring elements 6 such that the spring elements 6 are completely integrated into the interior of the claw members 2a, 2b of the clip 1 without protruding from the claw members 2a, 2b of the clip 1. It is observed in the variant depicted that both claw members 2a, 2b are provided with an opening 12, which can have an ogive shape, in which the spring elements 6 are inserted, one of the ends of the spring elements 9a being arranged against an edge of said opening 12 and the other end 9b in an indentation 11 made in a lobe 10 of the other claw member 2a, 2b. It is emphasized that both the openings 12 and the lobe 10 with the indentation 11 of both claw members 2a, 2b are symmetric, consequently both claw members 2a, 2b can be manufactured by means of the same mold by means, for example of injection, adding a pivot as an additional piece if necessary.

Figure 2:
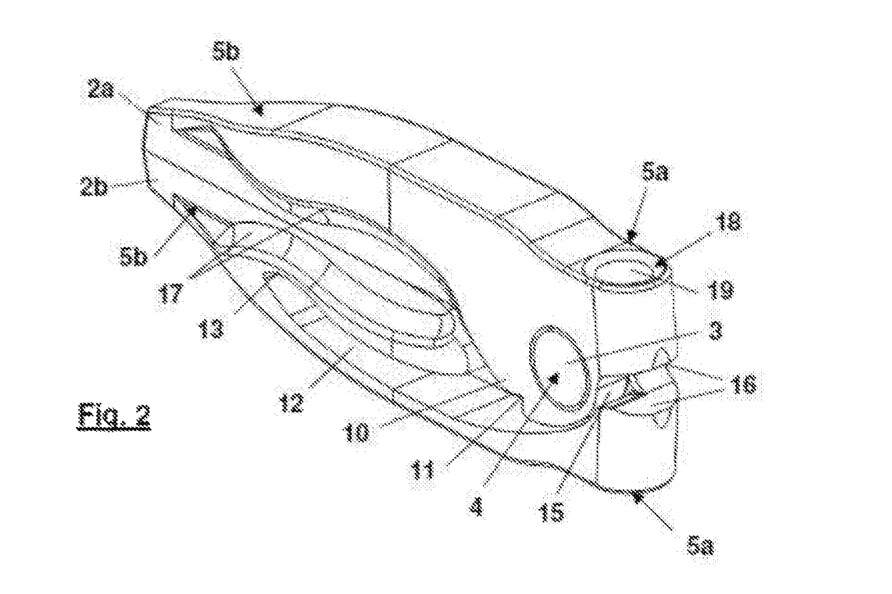
FIG. 2 depicts a perspective view of the claw members articulatedly joined to form the clip of the present invention.

The variant of the pair of claw members 2a, 2b shown in FIG. 1 is articulatedly joined to each other in the manner shown in FIG. 2. It is observed that the claw members 2a, 2b are provided with articulated joining means 3 which allow the rotation of the pair of claw members 2a, 2b around a pivot 4 which interlocks them. This articulated joining 3 is formed, in the variant depicted, by a rod 21 of one of the claw members, 2b which passes through a hole 22 of the other claw member 2a acting in the manner of a pivot 4, as is illustrated in the variant shown in FIGS. 1 and 2, the rod 21 is provided with retention means 23 in the manner of terminal expansion of the rod 21, to avoid the rod 21 being able to exit from the hole 22 after the pressured insertion thereof. It is also envisaged in other embodiments for both claw members 2a, 2b to be provided with holes 22 and the rod 21 is a separate element which can be inserted and maintain the pair of claw members 2a, 2b joined in an articulated manner to form the pivot 4 of the articulated joining 3, for example by means of a rivet. It is also envisaged that other joining means can be used, such as a thread which passes through both holes and is held by means of a corresponding counter thread maintaining the pair of claw members 2a, 2b articulatedly joined. It is also considered that in place of riveting the rod, it can be provided with end fastening pieces such as cotter pins or starlock washers.

Figure 3:
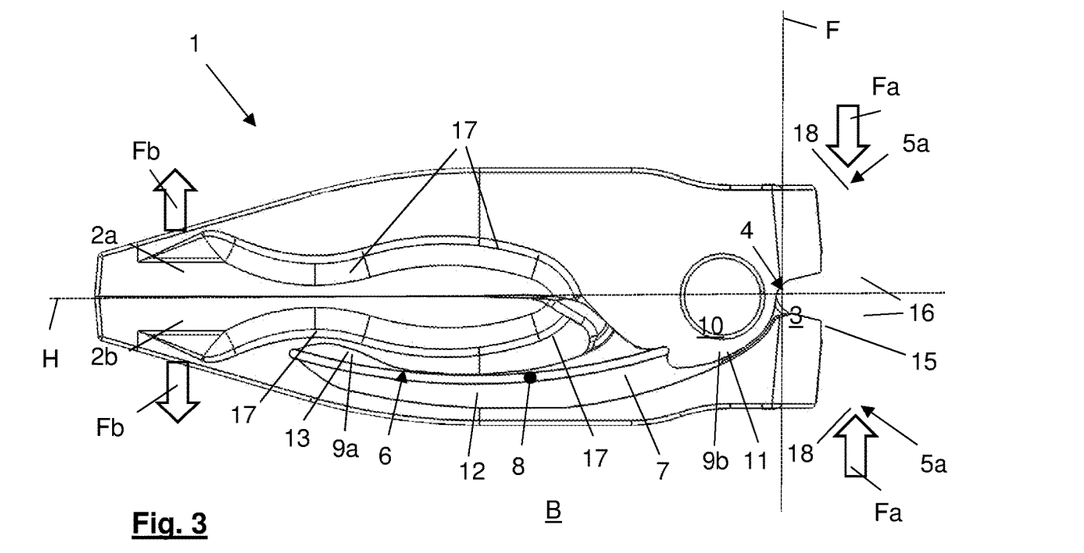
FIG. 3 shows a lateral view of the claw members articulatedly joined provided with spring elements forming a clip according to the present invention.

It is observed that the pair of claw members 2a, 2b comprise clamping surfaces which serve to tightly close the tissue and isolate the aneurism from the vessel, in the operative closed position B of the clip 1 as is illustrated further on, for example in FIG. 5c. These clamping surfaces are preferably rough such that a perfectly tight closure of the clip 1 on the tissue is achieved, thus isolating the part of the tissue with the aneurism from the rest of the tissue and preventing the clip from slipping. For example, the clamping surfaces can be complementary to each other and be provided with roughness in the form of peaks and troughs perpendicular to the longitudinal direction of the clip such as undulations or serrated teeth. It is observed in FIG. 2 that on each pair of claw members 2a, 2b, levers formed by a power arm 5a and a resistance arm 5b are distinguished, the pivot 4 acting in the manner of a fulcrum for both levers. In this way, after the insertion of the spring elements 6, as is illustrated in FIG. 3, the articulated joining means 3 allow the rotation of the pair of claw members 2, 2b around the pivot 4 which interlocks them, the clip 1 being able to adopt at least an opening position A, in which the resistance arms 5b of the claw members 2a, 2b are separated and a closure position B, in which the resistance arms 5b of the claw members 2a, 2b are applied to each other and are suitable for exerting a pressure sufficient for isolating an aneurism. The power arm 5a is defined as that on which an external force is applied and the resistance arm 5b as that which receives the force transmitted by the applicator.

In FIG. 3, it is observed that the spring elements 6 of the clip 1 comprise at least one flexible 7 and elastic element with a section with arced configuration 8, both in the opening position A and in the closure position B which is completely housed in the pair of claw members 2a, 2b without protruding from the profile of the clip 1. Said flexible element 7 has an arced shape without being a surpassed or horseshoe arc both in the opening position A and in the closure position B of the clip 1, that is, the curve thereof does not exceed 180° both in the opening position A and in the closure position B of the clip 1, thus allowing the functioning thereof in the manner of a leaf spring occupying a reduced space. It is also envisaged that a radiotransparent material, such as PEEK can be injected into the spring elements 6 to secure them on the clip 1.

It is also observed that the flexible element 7 is oblong and laminar and the opposed ends 9a, 9b thereof being retained on a different claw member 2a, 2b. In other embodiment variants, it is envisaged that the flexible element can also have other oblong shapes, such as in the shape of a rod. It is emphasized that the flexible element 7 is only in contact with the claw members 2a, 2b at the ends thereof. The variant shown in FIG. 3 is provided with two flexible elements 7 in arced laminar form, the frontal end 9a of each flexible element 7 being housed in an edge 13 of the opening 12 of a claw member 2a, 2b and the rear end 9b housed in the indentation 11 of the lobe 10 of the other claw member 2a, 2b such that the clip 1 has the same lateral view from one side as from the other.

The insertion of the flexible element 7 in the interior of the clip after joining the two claw elements 2a, 2b can be carried out by folding the flexible element 7 sufficiently until it can be introduced into the opening 12, being retained between the edge 13 of the opening 12 and the indentation 11 of the lobe when the flexible element 7 is released after the introduction thereof, forcing the closure position B of the clip 1 shown in FIG. 3. Alternatively, the flexible element 7 can be introduced by means of a rear separation channel 15 between the pair of claw elements 2a, 2b, in this way the flexible element 7 should be introduced until one of the opposed ends thereof 9a is applied against the edge 13 and continues forcing the flexible element such that it folds until the other opposed end thereof is applied against the opening 12. The use of this rear channel 15 is advantageous if the opening 12 is provided with lateral retention means 14 which prevent the flexible element 7 protruding laterally from the opening 12 in which it is housed and even the exiting thereof. Of course, these lateral retention means 14 can also allow the lateral entry of the flexible element 7 into the opening 12, however, not the exiting thereof, for example these being a tongue which could be folded sufficiently to allow the entry of said flexible element 7, but not the exiting thereof from the opening 12. However, if it is envisaged that the lateral retention means 14 are a band which passes completely through the opening 12, for example in a transversal manner, the clip 1 should be provided with the rear channel 15 for the introduction of the flexible element 7. Of course, when the clip 1 comprises two flexible elements 7, one arranged on each side of the clip 1, two rear channels 15 are required, one for each flexible element.

In FIG. 3, the horizontal H and vertical F cut planes of the clip 1, orthogonal to each other, are also illustrated, and they intersect in the center of the pivot 4, it being observed that the flexible elements 7 are placed, each one in the same quadrant in the closure position B. As will be seen below, the flexible elements 7 are maintained in place, each one in the same quadrant as in the closure position B when passing to the opening position A.

It is envisaged that both the material of the claw members 2a, 2b and of the spring elements 6 is biocompatible, that is to say, it allows the implantation thereof in the interior of the body of a patient. Of course, it is also considered that if some of the parts are not biocompatible, they can be housed or encapsulated in a biocompatible material such that they do not pose a risk.

The flexible element 7 which forms the spring elements 6 is preferably formed by a sheet of material with continuous carbon fiber, which allows sufficient force to be carried out to maintain the clip 1 closed, in addition to being resistant and biocompatible. In other embodiment variants, the use of a material with continuous carbon fiber with other shapes, such as rods, in the spring elements 6 is considered. Advantageously the flexible element 7 which forms the spring elements 6, when it is housed in the opening 12 without protruding, may not necessarily be biocompatible, in this way it is considered that the flexible element 7 can be made of materials not considered biocompatible such as fiber glass which has the appropriate mechanical properties. These materials not considered biocompatible could also be encapsulated in a biocompatible material, for example a biocompatible resin. Of course, it is envisaged that the spring elements 6 can also be made of other materials, such as polymers or fiber-reinforced polymers, if these have the appropriate mechanical properties.

A pair of rear arrows Fa are depicted in FIG. 3 which represent the external force which is carried out on the power arms 5a of the claw elements 2a, 2b to pass from the closure position B shown in FIG. 3 to the opening position A. This external force is preferably applied on respective support areas 18 formed by cups 19 as is explained below. In this way, by means of levers formed by the claw members 2a, 2b and the pivot 4, which acts in the manner of a fulcrum for the levers, a force is exerted on the resistance arms 5b of the claw members 2a, 2b, depicted by the pair of front arrows Fb to separate them and adopt an opening position A.

It is envisaged that the clip 1 is provided with stop surfaces 16, initially separated in the closure position B of the clip 1, in the manner illustrated in FIG. 3 and which are applied to each other in the opening position A, thereby limiting the opening of the clip 1, as will be seen below.

Figure 4:
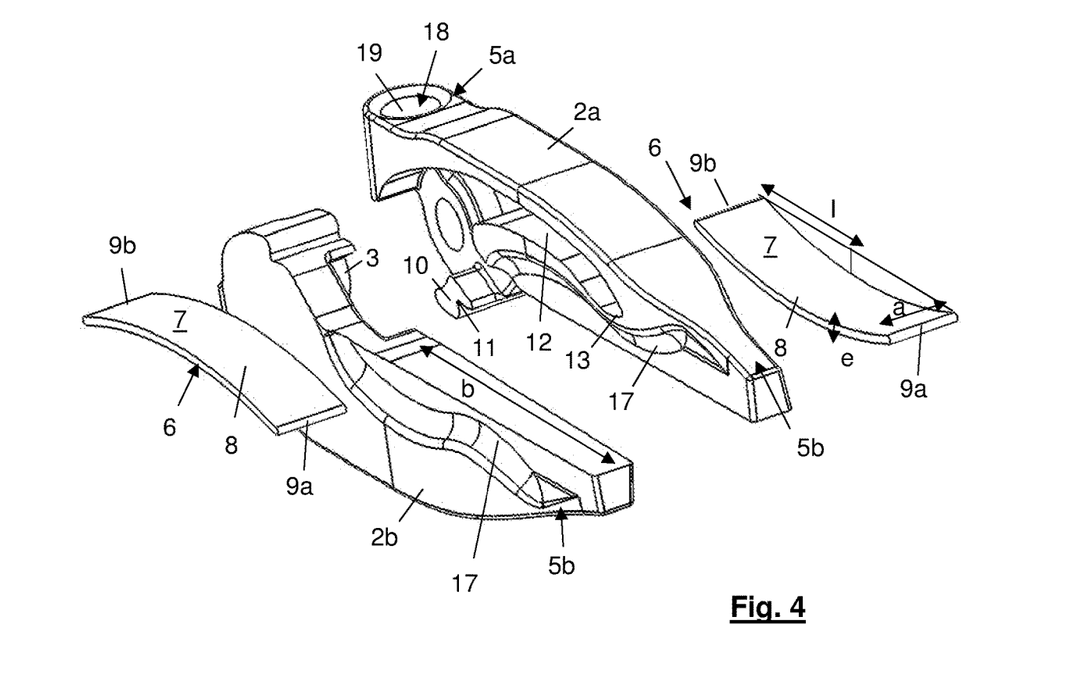
FIG. 4 depicts the clip of FIG. 3 in a correlative fitting position.

The clip 1 previously shown in FIG. 3 is illustrated in FIG. 4 now in the correlative fitting position, where it can be seen that the clip 1 is formed by two flexible elements 7 provided with a section with arced configuration 8 which is introduced into respective openings 12 provided on each one of the claw members 2a, 2b, the flexible elements 7 being arranged on each one of the sides of the clip 1 and placed symmetrically in the interior of the clip 1. In this way, it is observed that the clip 1 is symmetric.

Preferably, the sheets which form the flexible elements 7 are pre-tensioned and have at least one section with arced configuration 8. It is envisaged that the entire flexible element 7 forms a single section with arced configuration 8, although there can also be different arced sections or the flexible element can be provided with straight reinforcement ends. It is envisaged that both in the opening position A and in the closure position B of the clip 1, the intersection of the straight lines tangential to the ends of the section with arced configuration 8 of the flexible element 7 determine an angle α greater than 90 degrees such that the flexible element can be housed perfectly in the opening 12 of each claw member 2a, 2b without creating loops and acting in the manner of a spring in the shape of an arc, that is to say, a leaf spring. It is also observed that the section with arced configuration 8 of the flexible element 7 has the same direction of concavity both in the opening position A and in the closure position B of the clip 1, thus allowing the flexible element to be press-fitted between the claw members 2a, 2b at all times.

As has been previously introduced, the clip 1 is provided with support areas 18 formed by cups 19 for receiving an external force and passing from the closure position B to the opening position A, suitable for being placed in tissue. After placing the clip 1 on the aneurism, when the external force has been removed, it adopts the closure position B again, isolating the aneurism. These cups 19 determine the support areas 18 on the power arms 5a of the claw members 2a, 2b, adapted for cooperating with an applicator 100 such that the clip rotates from the closure position B to the opening position thereof A when the applicator exerts pressure on said support areas in the manner illustrated in FIG. 5a.

After joining the clip 1 and the applicator 100 such that the clip adopts the opening position A in which the stop surfaces 16 of the power arms 5a of the claw members 2a, 2b are applied to each other to limit the opening of the clip 1, the surgeon can place the clip 1 on the tissue. Advantageously, the clip 1 is provided with lateral recesses 17 on both sides to help the surgeon see, in addition to the thickness of the claw members 2a, 2b being less on the frontal end thereof than on the rear end thereof such that greater precision is achieved for carrying out a tight closure on the tissue to conveniently isolate an aneurism.

After placing the clip 1 appropriately on the tissue to be clamped, the surgeon actuates the applicator 100, progressively removing the external force which it exerts on the support areas and when the spring elements 6 exert force, after passing through the intermediate position shown in FIG. 5b, the clip 1 adopts the closure position B shown in FIG. 5c. At this point, the surgeon can completely release the applicator 100 from the clip 1 and remove it, the clip 1 being conveniently placed, carrying out a tight closure on the aneurism.

The flexible element 7 which forms the spring elements 6 must be dimensioned and placed on the clip 1 to allow the clip 1 to correctly maintain the aneurism closed when it adopts the closure position B. In order to achieve this tight closure of the aneurism, it is necessary for the clip 1 to carry out a closure force on the aneurism of approximately 180 grams when it adopts the closure position B which is shown in FIG. 5c.

In order to achieve this effect, the thickness (e) of the flexible element 7, the length of the clamping surface (l) of the clip 1 and the elastic module (E) of the material of the flexible element 7 should ideally comply with the following equation:

$$e = \sqrt[3]{\frac{b}{\beta E}}$$

where (β) is a geometric factor with value 7.5. Of course, it is envisaged that there is a range around the ideal values which allows the requirements of this closure force to be sufficiently satisfied. For improved identification, these dimensions have been indicated on the clip 1 and the flexible element 7 thereof previously described in FIG. 4.

The elastic module (E) depends on each material, this elastic module (E) being, by way of example 110 GPA for titanium, 210 GPA for stainless steel, 150 GPA for fiber-aligned Endolign; 9.4 GPA for Endolign perpendicular to the direction of the fiber and 18 GPA for PEEK 30 cf. The material is thus selected which allows a thickness (e) of the flexible element 7 to be obtained suitable for the length of the clamping surface (b) of the clip 1.

It is necessary for the dimensions of the flexible element 7 to allow for it to be maintained within the elastic range thereof at maximum opening, that is to say, when the clip 1 adopts the opening position A thereof such that the clip 1 bends to adopts the closure position B. It has been observed that this occurs when the width of the spring element is between 5 and 10 times the thickness of the spring element (e) and when the chord length of the arc of the flexible element 7 in the closure position B of the clip 1 is between 20 and 60 times the thickness of said spring element (e).

Taking into account the previous restrictions, considering a length of the clamping surface (b) of 9 mm and using fiber-aligned Endolign as the material, it is determined that a good compromise is obtained when the thickness (e) of the flexible element 7 is between 0.05 and 0.5 millimeters, thereby achieving the width (a) thereof to be less than 2 millimeters, for example between 0.25 and 2 millimeters and the chord length (l) thereof of arc to be between 4 and 12 millimeters. These dimensions allow the flexible element 7 to be able to be placed in a clip 1 with small dimensions, providing it with a sufficient closure force to maintain an aneurism closed and at the same time being maintained within the elastic range thereof at maximum opening. To reinforce this effect, it is preferable for the radius between the support point of the flexible element 7, which is the indentation 11 of the lobe 10, and the center of the rotational pivot 4 of the clip 1 to be between 0.5 and 3 millimeters.

Figures 6A, 6B:
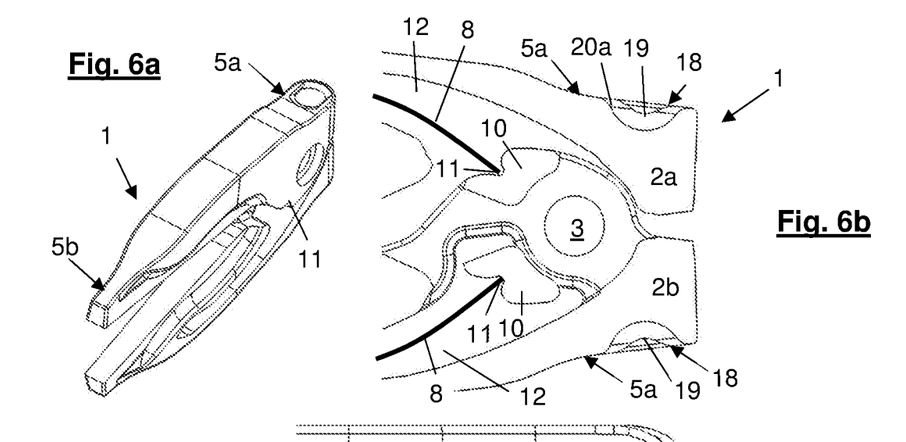
FIGS. 6a to 6c show a detail of the cup of the clip of the present invention.
Figure 6C:
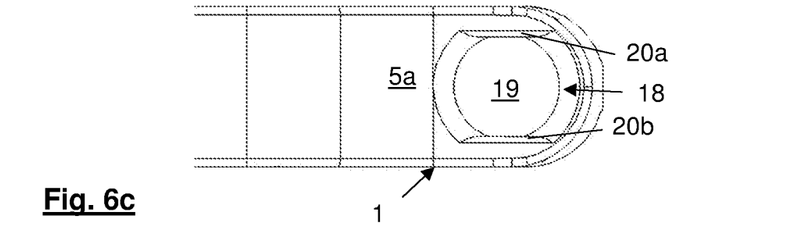
Figure 7A:
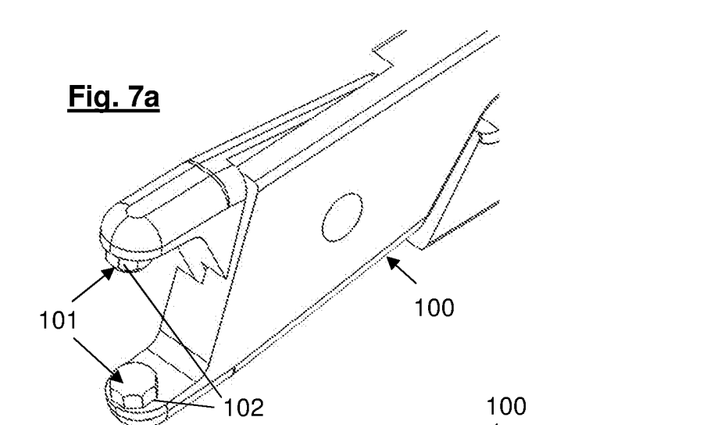
FIGS. 7a and 7b show a detail of the end of an applicator for the clip of the present invention.
Figure 7B:
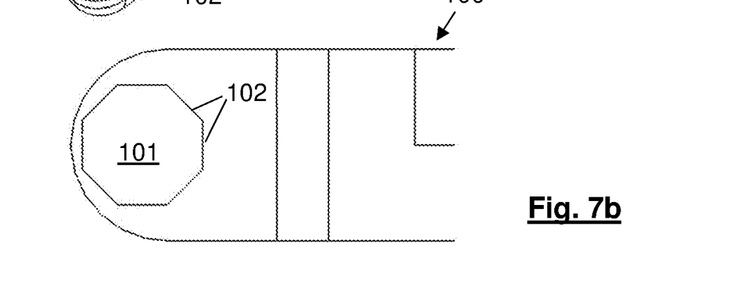

FIGS. 6a, 6b and 6c show details of the clip 1 in which it is observed that the cup 19 is advantageously provided with two straight parallel surfaces 20a, 20b adapted for receiving an essentially hemispheric end 101 of the applicator 100, the applicator 100 being provided with a set of straight parallel faces 102 which form a polygonal prism as is illustrated in FIGS. 7a and 7b such that the clip 1 can be arranged in different orientations according to how the two straight parallel surfaces 20a, 20b of the clip 1 are arranged against the essential hemispheric end 101 of the applicator 100. In the variant illustrated, in which the set of straight parallel faces 102 of the applicator 100 form an octagon, the clip can be arranged, in addition to being aligned with the applicator, rotated 45 degrees or 90 degrees to the right or left. Of course, it is envisaged to be able to use polygons with more faces to allow more granularity in the angles which the clip 1 can adopt in relation to the applicator 100.

It is envisaged that the different variants of the clip 1 can be provided with one or a plurality of pieces marked with a material opaque to X-rays or other radiations used for obtaining images such that the presence of the clip can be clearly identified in an image taken. This marked piece can be, for example a microsphere or a metal filament embedded in at least one of the claw members 2a, 2b. It is also envisaged that the marked piece can be a washer 4w inserted between the two claw members 2a, 2b or that the same pivot 4 is metallic, thus acting in the manner of the marked piece.

The marked piece can be a metal inlay in at least one of the two claw members 2a, 2b applied by means of ultrasound. It is also envisaged that the claw 1 can be provided with loads of a material radiopaque to X-rays, such as radiopaque compounds mixed with the polymer during some of the manufacturing steps of the clip 1.

It is also emphasized that in FIG. 6b, which depicts a lateral cut view of the clip 1, the openings 12 and indentations 11 of each claw member 2a, 2b can be observed which house each one of the two flexible elements 7 of the clip 1. In this cut view, the symmetry of the clip 1 can be observed which may be hidden in the other figures.

Figure 8:
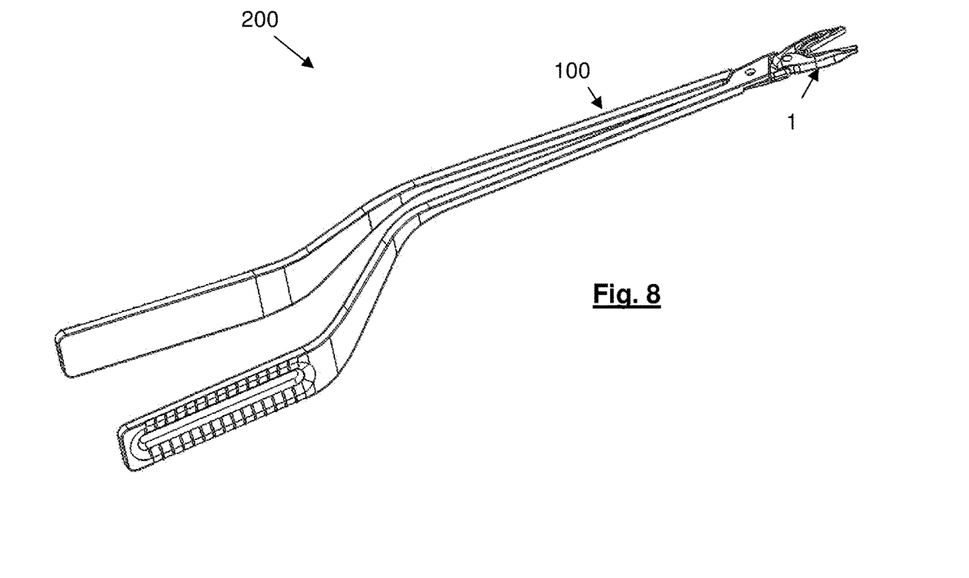
FIG. 8 shows the clip mounted on an applicator.

It is envisaged that the separation between the two straight parallel surfaces 20a, 20b of the cup 19 of the clip 1 is greater than the separation between the straight parallel faces 102 of the essentially hemispheric end 101 of the applicator 100 such that after coupling the clip 1 into the applicator 100 forming the kit 200 shown in FIG. 8, the surgeon can modify the rotation of the clip 1 with respect to the applicator 100 exerting certain pressure on the clip 1 such that if, for example the applicator 100 is the one previously shown in FIGS. 7a, 7b, and the clip 1 is initially aligned with the applicator, a stable position can be obtained with an inclination of 45 degrees and if certain pressure continues to be exerted, the inclination achieved is 90 degrees. Of course, the separation between the two straight parallel surfaces 20a, 20b of the cup 19 of the clip 1 should be calculated so that this optional effect of rotation can be achieved without affecting the stability of the position of the clip 1. It is also possible to design the kit 200 of the clip 1 and applicator 100 devoid of this rotation effect, the support areas 18 of the clip 1 being, for example compatible with the known applicators like the one shown in FIG. 9.

Figure 9:
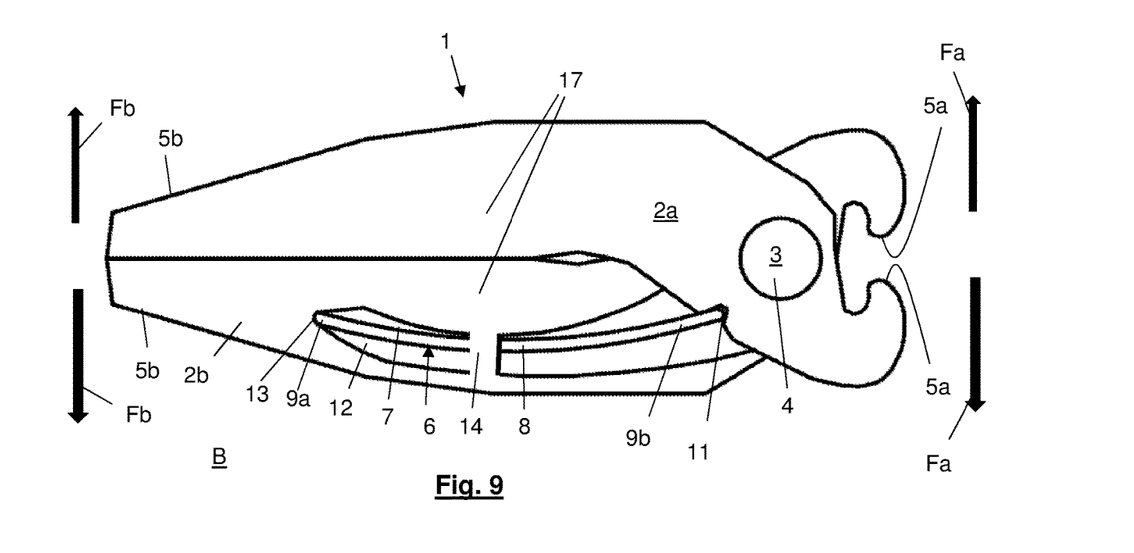
FIG. 9 depicts another embodiment variant of the clip.

FIG. 9 shows an alternative embodiment variant of the clip 1, in which unlike the previous variant shown in FIG. 3, the claw members 2a, 2b intersect, thus allowing the opening direction of the resistance arm 5b of each claw member 2a, 2b to match the direction of the force applied on the corresponding power arm 5a thereof. In this way, a variant of the clip 1 provided with joining teeth on the rear part thereof is achieved suitable for the use thereof with the known applicators. Lateral retention means 15 are also illustrated in the variant shown in FIG. 9 in the form of a band which passes through the opening 12 and prevents the flexible element 7 from protruding.

Figure 10:
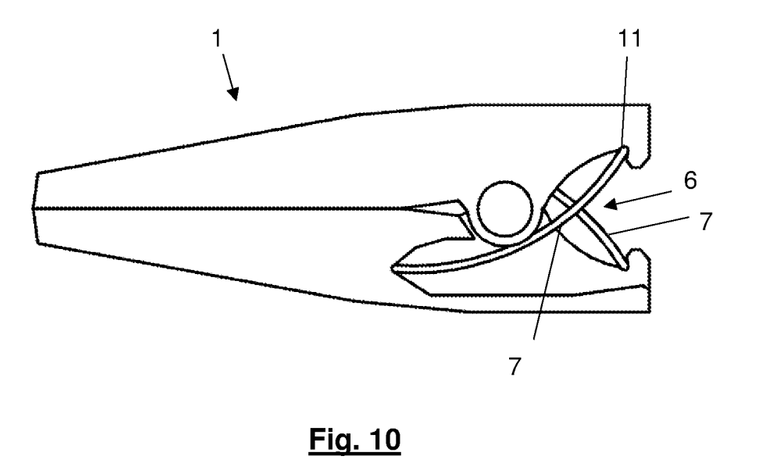
FIGS. 10 and 11 show other embodiment variants of the clip.
Figure 11:
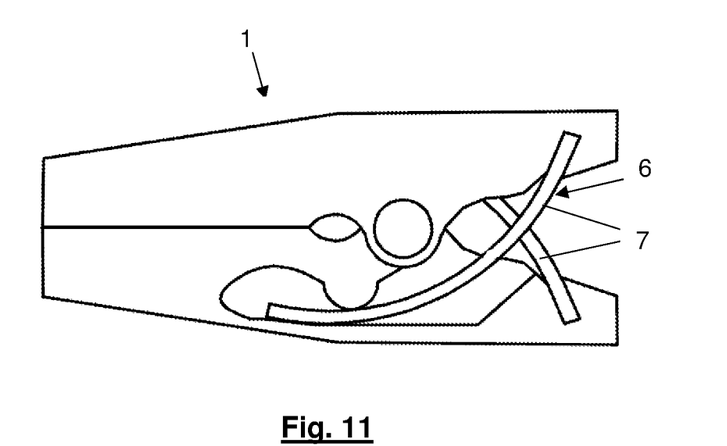

FIG. 10 shows an alternative embodiment variant of the clip 1 in which the flexible element 7 reaches the rear end of the members on which the indentation 11 is located. FIG. 11 shows another variant of the clip similar to the one of FIG. 10 in which the flexible element is over-injected into one of the claw members. In the variants of FIGS. 10 and 11, the flexible element 7 of the spring elements 6 are partially housed in the clip and press-fitted without protruding from the profile of the clip 1, that is to say, from the volume in which the clip 1 is contained, specifically the pair of interlocked claw members 2a, 2b.

FIGS. 12 to 17 show other clips 1 for aneurisms.

Figure 12:
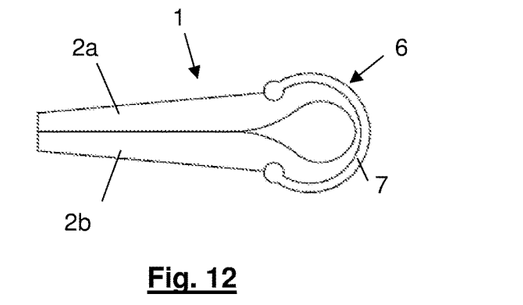
FIGS. 12 to 17 show other clips for aneurisms.

FIG. 12 shows a clip 1, the claw members 2a, 2b thereof are formed by a single piece, the clip 1 being provided with exterior spring elements 6 formed by a flexible element 7 in the shape of a C orientated towards the frontal part of the clip which surrounds the rear part thereof. In another clip, the two claws could be joined by means of a pin, the spring elements 6 passing through the two claws in the central part.

Figure 13:
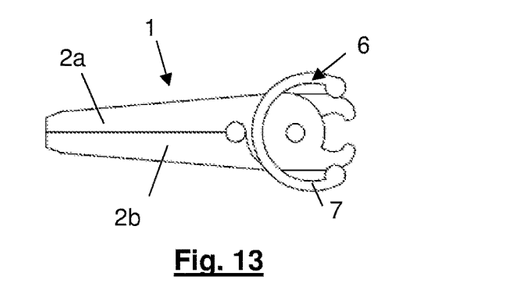

FIG. 13 shows another clip 1 provided with a spring element 6 formed by a flexible element 7 in the shape of a C which protrudes from the claw members 2a, 2b. The spring element 6 can be soldered in a lateral of the clip or introduced into the clip, where the claws 2a, 2b would be provided with a housing where the spring elements are introduced. The opening of this clip would be carried out when an applicator exerts an opening force on the rear part.

Figure 14:
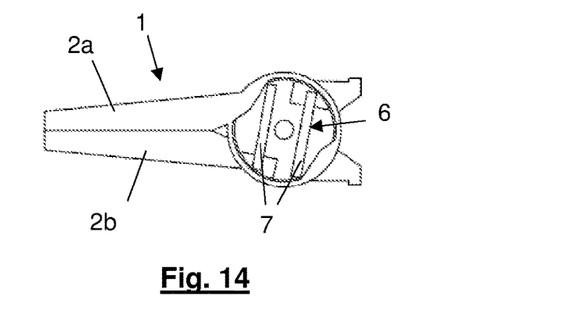

FIG. 14 shows another clip 1 in which the spring elements 6 which are flexible elements 7 are housed in the claw members 2a, 2b, the spring elements 6 adopting a straight position in the closure position shown in FIG. 14. In this clip 1, the two spring elements 6 are fixed on one claw member 2a at one of the ends thereof, while the other end is free and applied against the other claw member 2b. In this way, the free end of the spring element 6 rubs with a cam geometry which allows the force to be exerted on the claw member 2b on which it is applied when the clip 1 is opened.

Figure 15:
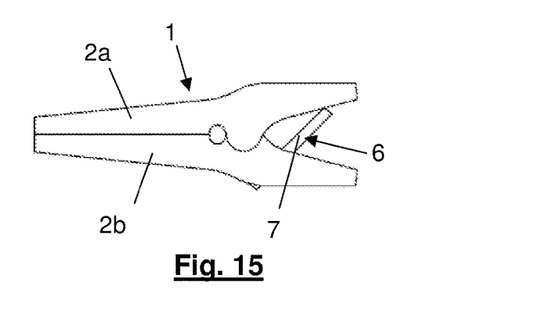

FIG. 15 shows another clip 1 on which the spring elements 6 formed by a flexible element 7 are fixed on one of the claw members 2b and are applied against the other claw member 2a, the spring means adopting a straight position in the closure position shown in FIG. 14.

Figure 16:
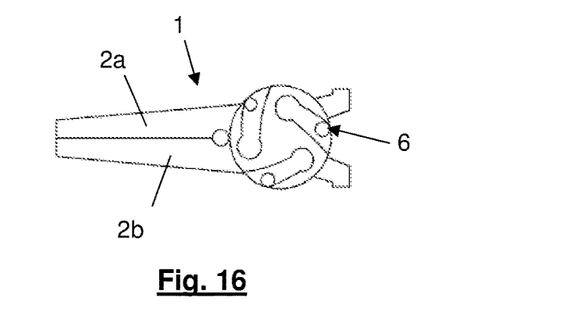

FIG. 16 shows another clip 1 on which the spring elements 6 are formed by the claw members 2a, 2b, that is to say, they have been molded together with the claw members 2a, 2b, consequently they are made of the same material. In this clip, the claw 2a is provided with pins which interact with the tabs of the claw 2b causing force to be exerted on the claws of the clip.

Figure 17:
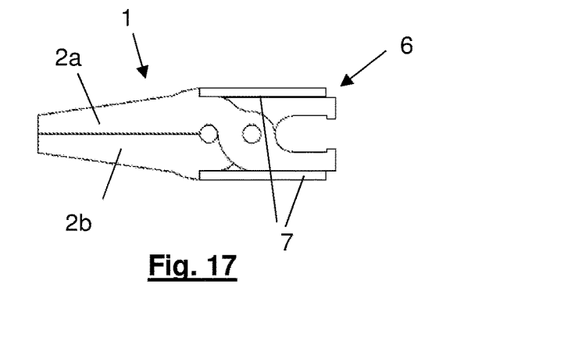

FIG. 17 shows another clip 1 in which the spring elements 6 are flexible elements 7 which are adhered on the external part of the claw members 2a, 2b. In this case, flexible elements 7 are anchored on the frontal part of the clip and are free on the rear part thereof, allowing it to be able to be arced towards the exterior during the opening of the clip 1, thus producing a closure force.

The invention claimed is:

1. A clip (1) for an aneurism which comprises a pair of claw members (2a, 2b) made of non-metallic material and means for the articulated joining (3) of the claw members which allows the rotation of the pair of claw members around a pivot (4) which interlocks the pair of claw members, a power arm (5a) and a resistance arm (5b) being distinguished on each claw member, configured such that the clip can adopt at least:
    an opening position (A), in which the resistance arms of the claw members are separated from each other; and
    a closure position (B), in which the resistance arms of the claw members are applied to each other;

the clip being provided with two separate spring elements (6) each spring element bends to arrange the clip in the closure position, wherein each spring element is at least partially housed in the clip and comprises a flexible and elastic portion with a section with arced configuration (8), each spring element is press-fitted with two opposing ends (9a, 9b), each of the two opposing ends exerting pressure on a different claw member both in the opening position and in the closure position; and wherein each flexible and elastic portion is housed at least partially in a corresponding claw member.

2. The clip (1) according to claim 1, wherein at least one spring element (6) is completely housed in the clip.

3. The clip (1) according to claim 1, wherein at least one of the flexible and elastic portions (7) has an arced shape without being a surpassed arc, that is, the curve thereof does not exceed 180°.

4. The clip (1) according to claim 1, wherein at least one of the flexible and elastic portions (7) is oblong, the opposed ends (9a, 9b) of the flexible element being retained on a different claw member (2a, 2b).

5. The clip (1) according to claim 1, wherein at least one of the flexible and elastic portions (7) is laminar.

6. The clip (1) according to claim 5, wherein a thickness (e) of at least one of the flexible and elastic portions (7), a length of a clamping surface (b) of the clip and an elastic module (E) of the material with which the at least one of the flexible and elastic portions is manufactured are related by the expression:

$$e = \sqrt[3]{\frac{b}{\beta E}}$$

where (β) is a geometric factor with value 7.5.

7. The clip (1) according to claim 1, wherein a width (a) of the at least one of the flexible and elastic portions (7) is between 5 and 10 times the thickness (e) thereof and a chord length (I) of the arc of the flexible element in the closure position (B) is between 20 and 60 times the thickness thereof.

8. The clip (1) according to claim 1, wherein a thickness (e) of at least one of the flexible and elastic portions (7) is between 0.5 and 0.05 millimeters, a width (a) of the at least one of the flexible and elastic portions (7) is less than 2 mm and a chord length (I) of the arc of the at least one of the flexible and elastic portions in the closure position (B) is between 4 and 12 millimeters.

9. The clip (1) according to claim 1, wherein a radius (r) between a support point of at least one of the flexible and elastic portions (7) and a center of the rotational pivot (4) is between 0.5 and 3 millimeters.

10. The clip (1) according to claim 1, wherein each one of the claw members (2a, 2b) is formed by a single piece.

11. The clip (1) according to claim 1, wherein considering horizontal (H) and frontal (F) cut planes thereof, orthogonal to each other and which intersect in the center of the pivot (4), at least one of the flexible and elastic portions (7) is placed in a same quadrant both in the opening position (A) and in the closure position (B).

12. The clip (1) according to claim 1, wherein one of the claw members (2a, 2b) comprises a lobe (10), one of the opposed ends (9a, 9b) of one of the flexible and elastic portions (7) being retained in an indentation (11) of the perimeter of the lobe.

13. The clip (1) according to claim 1, wherein at least one of the claw members (2a, 2b) comprises an opening (12), configured as a groove which receives and houses a corresponding flexible element (7).

14. The clip (1) according to claim 13, wherein the opening (12) is provided with an edge (13) for retaining one of the opposed ends (9a, 9b) of at least one of the flexible and elastic portions (7).

15. The clip (1) according to claim 1, wherein the claw members (2a, 2b) are provided with clamping surfaces complementary to each other and provided with roughness in the form of peaks and troughs perpendicular to the longitudinal direction of the clip.

16. The clip (1) according to claim 15, wherein an opening (12) is provided with lateral retention means (14) to prevent at least one of the flexible and elastic portions (7) from protruding laterally from said opening in which it is housed.

17. The clip (1) according to claim 1, comprising a rear channel (15) between the claw members (2a, 2b) for the introduction of at least one of the flexible and elastic portions (7).

18. The clip (1) according to claim 1, wherein the power arms (5a) of the claw members (2a, 2b) comprise stop surfaces (16) adapted for being applied to each other in the opening position (A) and separated in the closure position (B).

19. The clip (1) according to claim 1, wherein both in the opening position (A) and in the closure position (B), the intersection of straight lines tangential to ends of the arced configuration (8) of at least one of the flexible and elastic portions (7) determine an angle greater than 90 degrees.

20. The clip (1) according to claim 1, wherein the material of the claw members (2a, 2b) and of the spring means (6) is biocompatible.

21. The clip (1) according to claim 1, wherein the section with arced configuration (8) of at least one of the flexible and elastic portionsthe flexible element (7) has a same direction of concavity both in the opening position (A) and in the closure position (B) of the clip.

22. The clip (1) according to claim 1, wherein the flexible element (7) comprises a material with continuous carbon fiber.

23. The clip (1) according to claim 1, comprising material opaque to X-rays on at least one claw member (2a, 2b).

24. The clip (1) according to claim 23, wherein the material opaque to X-rays are uniformly distributed on the at least one claw member (2a, 2b).

25. The clip (1) according to claim 24, comprising a piece marked with a material opaque to X-rays.

26. The clip (1) according to claim 25, wherein the marked piece comprises a microsphere embedded in at least one of the claw members (2a, 2b).

27. The clip (1) according to claim 25, wherein the marked piece comprises a metal filament embedded in at least one of the claw members (2a, 2b).

28. The clip (1) according to claim 25, wherein the marked piece comprises a washer inserted between the two claw members (2a, 2b).

29. The clip (1) according to claim 25, wherein the marked piece is the pivot (4).

30. The clip (1) according to claim 25, wherein the marked piece is a metallic inlay on at least one of the two claw members (2a, 2b).

31. The clip (1) according to claim 1, comprising lateral recesses (17) on both sides in order to see more easily.

32. A kit (200) formed by a clip (1) according to claim 1 and an applicator (100) for articulating said clip, wherein the clip comprises support areas (18) on the power arms (5*a*) of the claw members (2*a*, 2*b*) adapted for cooperating with the applicator (100) such that the clip rotates from the closure position (B) to the opening position (A) thereof when the applicator exerts pressure on said support areas.

33. The kit (200) according to claim 32, wherein at least one of the support areas (18) of the clip (1) comprises a cup (19) provided with two straight parallel surfaces (20a, 20b) adapted for receiving an essentially hemispheric end (101) of the applicator (100) provided with a set of straight parallel faces (102).

34. The kit (200) according to claim 33, wherein separation between the two straight parallel surfaces (20*a*, 20*b*) of the cup (19) of the clip (1) is greater than separation between the straight parallel faces (102) of the essentially hemispheric end (101) of the applicator (100).

* * * * *